United States Patent [19]

Arretz

[11] Patent Number: 4,927,972
[45] Date of Patent: May 22, 1990

[54] CATALYTIC PROCESS FOR THE PRODUCTION OF MERCAPTANS FROM THIOETHERS

[75] Inventor: Emmanuel F. E. Arretz, Pau, France

[73] Assignee: Societe Nationale Elf Aquitaine (Production), Courbevoie, France

[21] Appl. No.: 284,767

[22] Filed: Dec. 12, 1988

Related U.S. Application Data

[63] Continuation of Ser. No. 93,640, Sep. 8, 1987, abandoned.

[30] Foreign Application Priority Data

Sep. 11, 1986 [FR] France ................................. 8612690

[51] Int. Cl.$^5$ ............................................ C07C 148/00
[52] U.S. Cl. ...................... 568/70; 260/399; 562/606; 568/59
[58] Field of Search ..................... 568/67, 68, 70, 58, 568/59, 60; 260/399; 562/606

[56] References Cited

U.S. PATENT DOCUMENTS 2,831,031  4/1958  Binning et al. ...................... 568/70
3,069,472 12/1962  Loev et al. ............................ 568/68
3,376,348  4/1968  Stratton ................................ 568/59
4,005,149  1/1977  Kubicek .............................. 568/68
4,059,636 11/1977  Kubicek .............................. 568/70
4,102,931  7/1978  Buchholz ............................ 568/73
4,278,816  7/1981  Shim .................................... 568/67
4,313,006  1/1982  Hager .................................. 568/70

FOREIGN PATENT DOCUMENTS 0047021 10/1982  European Pat. Off. .
70-05531  2/1970  Japan .................................... 568/68

Primary Examiner—Mary E. Ceperley
Attorney, Agent, or Firm—Stevens, Davis, Miller & Mosher

[57] ABSTRACT

A catalytic process for the production of mercaptans from thioethers, which comprises reacting a thioether, in which the sulfur atom of the thioether function is bonded, on the one hand to a tertiary carbon atom and, on the other hand, to a primary or secondary carbon atom, with hydrogen sulfide in the presence of an appropriate acid catalyst, especially an aluminosilicate or an ion-exchange resin.

11 Claims, No Drawings

CATALYTIC PROCESS FOR THE PRODUCTION OF MERCAPTANS FROM THIOETHERS

This application is a continuation of application Ser. No. 093,640, filed Sept. 8, 1987, now abandoned.

BACKGROUND OF THE INVENTION

1. Field of the Invention

The present invention relates to the production of mercaptans from thioethers and hydrogen sulfide in the presence of appropriate catalysts.

2. Background Art

The industrial interest in mercaptans is such that numerous studies have been conducted with a view to perfecting synthesis of these compounds. The processes most widely used in practice are based on the reaction of $H_2S$ with alcohols or with olefins. In the majority of cases, the main by-products obtained are thioethers, formed mainly by reaction of the mercaptans with the alcohols or with the olefins, depending on the process used. Aside from a small number of thioethers, the symmetric thioethers obtained in the synthesis of mercaptans generally have no commercial value.

Methods of conversion of these thioethers have been proposed to transform them into corresponding mercaptans by reaction with hydrogen sulfide in the presence of different catalysts.

However, despite certain improvements achieved (more efficient catalysts, introduction of carbon disulfide as promotor . . . ), these reactions necessitate elevated temperatures (250° to 360° C.) and lead to the formation of undesirable by-products, which have the consequence of appreciably lowering the mercaptan selectivity.

The present invention provides a new process, the principal advantages of which are very high mercaptan yield and selectivity, and the possibility of obtaining easily primary and secondary mercaptans.

SUMMARY OF THE INVENTION

This invention relates to a catalytic process for the production of mercaptans from thioethers, which comprises reacting a thioether, in which the sulfur atom of the thioether function is bonded, on the one hand, to a tertiary carbon atom and, on the other hand, to a primary or secondary carbon atom, with hydrogen sulfide in the presence of an appropriate acid catalyst.

DETAILED DESCRIPTION

The process according to the invention is characterized in that $H_2S$ is made to react with a thioether (formula A below), the S atom of which is bonded to a tertiary carbon atom and to a primary or secondary carbon atom. The reaction takes place in the presence of an appropriate acid catalyst, at a temperature between room temperature and 200° C., advantageously above 80° C., preferably under pressure. The thioether is in the liquid or gaseous state.

Sulfhydrolysis is analogous to hydrolysis but utilizes $H_2S$ in place of $H_2O$. The sulfhydrolysis of the thioether according to the invention can be represented by the reaction:

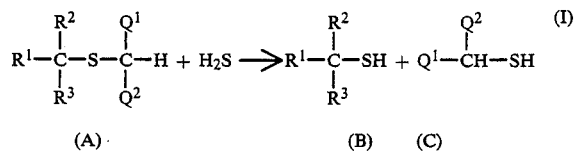

where $R^1$, $R^2$, and $R^3$, which can be alike or different, are hydrocarbon, notably alkyl, cycloalkyl and/or aryl groups, the carbon atom bearing them thus being tertiary. Symbols $Q^1$ and $Q^2$ can represent hydrocarbon groups, but one of them can also be a hydrogen atom or bear one or a plurality of functional groups.

Starting from the thioether (A), there is therefore obtained a tertiary mercaptan (B) and a mercaptan (C), which can be primary or secondary depending on the nature of the Groups Q.

This new reaction affords vast synthesis possibilities. If an economic source of thioether (A) is available and the two mercaptans (B) and (C) find uses, these two products can be collected at the same time. A very interesting alternative synthesis of the compound (C) alone comprises resulting (B) to recreate the thioether (A) from an olefin

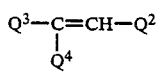

by the reaction:

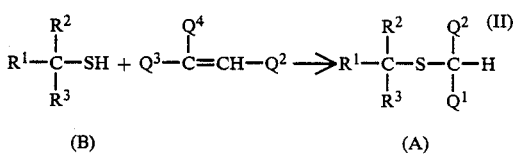

$Q^1$ representing

where $Q^3$ and $Q^4$ are hydrogen atoms or hydrocarbon groups.

Depending on the type of thioether (A), the synthesis thereof is realized either by a free-radical and/or photochemical process or by a reaction of heterogeneous catalysis.

The production of thioether (A) can also be envisioned by other known synthesis routes, depending on the technical and economic interest of using raw materials other than olefins, in other words halogenated derivatives, alcohols, etc. This can therefore be used cyclically, with advantageous production of mercaptan (C), by means of the two reactions which have just been described and which in practice are realized in the successive order of (2) and then (1).

Although the new process could be realized with compounds having various groups $R^1$, $R^2$, $R^3$, and $Q^1$, $Q^2$, $Q^3$, $Q^4$, the most commonly selected groups $R^1$ to $R^3$ are chosen from $C_1$ to $C_{24}$ hydrocarbons and especially $C_1$ to $C_{18}$ alkyl groups and/or from the $C_5$ to $C_{10}$ cycloalkyl and aryl groups which can bear alkyl substituents. The same is true for groups $Q^1$ to $Q^4$, except that a plurality of those can be hydrogen atoms or bear functional groups, such as CN, COOH, OH, NH₂, halogen, ester, ether oxide, amide, nontertiary S, sulfoxide, sulfone, etc.

When the cyclic process is used, it is desired to choose groups $R^1$ to $R^3$ such that mercaptan (B), that is, $R^1R^2R^3$—C—SH, has a boiling point sufficiently different from that of the mercaptan (C) to be prepared, $Q^1Q^2$CH—SH, that separating them by distillation is easy.

Thus, for example, it is possible by means of the invention to realize almost quantitatively a reaction such that:

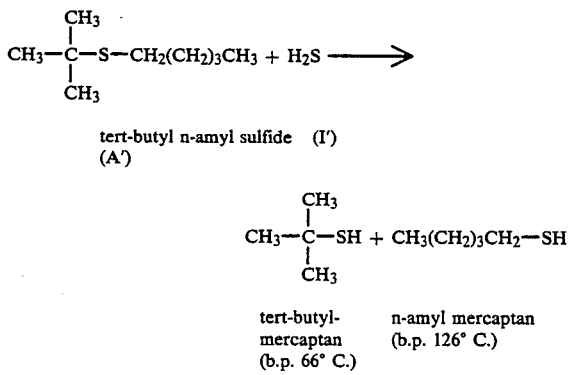

It is therefore easy to separate these two compounds by distillation and to use the first to recreate the starting sulfide (thioether) by a photochemical or free-radical reaction:

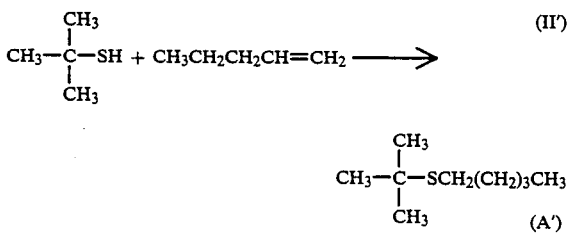

The thioether (A') is used once again for the production of n-amylmercaptan by reaction (I'), and so on.

The catalysts preferred for the present invention are natural and synthetic aluminosilicates, such as the zeolites, or also highly acid ion-exchange resins. Among the natural aluminosilicates are the silica-alumina products having alumina contents of 1 to 20%, such as those which the DAVISON CHEMICAL Company produces, or also acid montmorillonite derivatives, with the general structure:

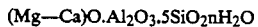

the trade name of which is FILTROL.

The zeolites in question are preferably the types X or Y with alkali metal contents lower than 15% in the form of $Na_2O$ and more advantageously of less than 3 weight percent of alkali metal.

The acid ion-exchange resins in question are cation exchangers; they are of aromatic polymeric structure or perfluorinated aliphatic structure, containing sulfonic acid groups and being able to be used in bulk or fixed to a mineral or organic support.

These polymeric materials can be based on polystyrene and divinylbenzene. In this case, these products are sulfonic acid resins, which are commercially available under the names of Amberlite, Amberlyst, Lewatit, Dowex, Duolite. Regarding the perfluorosulfonic acids, they are sold by DU PONT DE NEMOURS under the name of NAFIONS.

Phosphoric acid impregnating a support can be also used as a convenient catalyst.

As indicated above, the sulfhydrolysis (I) according to the invention is conducted at temperatures between about room temperature and 200° C. (preferably above 80° C.), depending on the nature of the thioether treated. In the most common cases, in which this thioether has approximately 6–24 carbon atoms, the optimum temperature lies between about 100° C. and 180° C. and particularly between 110° C. and 155° C.

Depending on the circumstances, the duration of contact of the thioether and of the $H_2S$ with the catalyst generally varies between about 15 and 120 minutes.

The reaction can be realized under only slight pressure, but, to appreciably improve production and avoid secondary reactions, it is beneficial to operate under higher pressures, notably under about 5 to 30 bar, and especially under 10 to 20 bar.

It is advantageous in conducting the process of the invention to operate with a certain excess of $H_2S$ relative to the stoichiometric quantity of thioether. Thus, it can be recommended to operate with about 1 to 6 mole of $H_2S$ per mole of thioether used, and especially with 2 to 4 mole of $H_2S$.

In the most preferred embodiment of the invention, a homogeneous or heterogeneous mixture of $H_2S$ with the thioether in the vapor or liquid state passes through the catalyst charge placed in a reactor. It is maintained at the desired temperature and pressure.

The products obtained after contact of the reagents on these catalysts are generally subjected to fractional distillation. In the cyclic process, the tertiary mercaptan formed is recycled to the reactor for thioether production, while the unconverted thioether is returned to the inlet of the sulfhydrolysis reactor to be retreated. Under the conditions of the present invention, primary or secondary mercaptans can be obtained with a purity higher than 99%.

The following examples are not considered limiting. They demonstrate the possibilities offered by the present invention and the practical interest of the new process.

EXAMPLE 1

Simultaneous preparation of tert-butylmercaptan and n-dodecylmercaptan

There is used a tubular reactor of 25 mm diameter, having a useful capacity of 200 ml, charged with 200 ml of previously dried cation-exchange resin known under the trade name of AMBERLYST 15. Through this charge there is passed, per hour: 84 g of thioether comprising tert-butyl n-dodecyl sulfide, $(CH_3)_3C$—S—$CH_2(CH_2)_{10}CH_3$, and 45 g of $H_2S$, (that is, 4 mole of $H_2S$ per 1 of mole sulfide).

The pressure in the reactor is maintained at 15 bar, and the temperature is controlled at 110° C.±2° C. by the circulation of oil maintained at constant temperature and passing through a double jacket which surrounds the reactor.

The analysis of the raw products of the reaction shows that the transformation of the starting thioether is 65% and yields exclusively tert-butylmercaptan, (CH₃)₃C—SH and n-dodecyl mercaptan, CH₃(CH₂)₁₀CH₂—SH. The latter compound is produced at 43 g/hr, with a selectivity of practically 100%.

EXAMPLE 2

Cyclic reuse of the tertiary mercaptan

The products obtained following the operation of Example 1 are separated from each other by distillation, which is facilitated by the substantial difference between the boiling points thereof.

After recovery of the n-dodecyl mercaptan as a desired synthesis product, the tert-butylmercaptan is passed into a photochemical reactor in the following manner.

The reactor comprises a stainless-steel cylinder with a useful volume of 300 ml. In the axis of this cylinder, there is fixed coaxial quartz tube, containing a mercury lamp with an emission maximum at the wavelength of 350 nm. Cooling and agitation of the reaction medium are ensured by an external loop, comprising a recirculation pump and a heat exchanger, permitting the temperature of the medium to be maintained at 20° C.±2° C.

Into the reactor there is continuously introduced, per hour, 135 g of tert-butylmercaptan (CH₃)₃C—SH, that is, 1.5 mole, and 168 g of 1-dodecene, that is, 1 mole, with additions of $2.2 \times 10^{-3}$ mole of benzophenone and $0.6 \times 10^{-3}$ mole of tributyl phosphite. The flow rate of liquid exiting the reactor is measured. The excess mercaptan and the untransformed dodecene are removed by distillation. The weight of thioether formed by the reaction

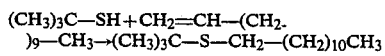

is 129 g per hour, corresponding to a yield of 50% relative to the dodecene used. This thioether is used in the process of Example 1 for the production of n-dodecyclmercaptan. This operating cycle is repeated 10 times. In this way, n-dodecyl mercaptan is obtained with a mean dodecene transformation ratio of 77.9% and with a selectivity of 99% relative to this olefin.

EXAMPLE 3

Use of an aluminosilicate catalyst

The operations of Example 1 are repeated with an acid montmorillonite derivative of the structure (Mg—Ca)O.Al₂O₃.-5SiO₂.nH₂O, known in industry under the name FILTROL. 200 ml of this catalyst is placed in the reactor instead of the AMBERLYST.

The thioether transformation ratio was 59%, and the mercaptans obtained are as pure as in Example 1.

EXAMPLE 4

Sulfhydrolysis of n-butyl tert-octyl sulfide

The thioether corresponding to this example is synthesized by free-radical addition of tert-octyl mercaptan, a product obtained commercially, to 1-butene. The purpose of the sulfhydrolysis reaction is to transform this thioether into two mercaptans: tert-octyl mercaptan and n-butyl mercaptan, according to the reaction:

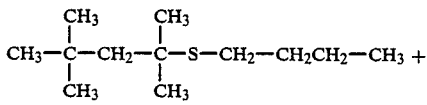

-continued

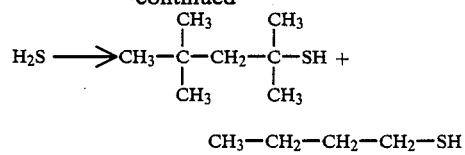

The operating conditions of Example 1, that is, 110° C., 15 bar and 200 ml of AMBERLYST resin as catalyst, are applied to the reaction. The hourly flow rate of ether is 34 g and that of H₂S 45 g (that is, 4 H₂S per mole of thioether).

In this way, the n-butylmercaptan, CH₃CH₂CH₂CH₂SH is obtained with a selectivity of practically 100%, at a rate of 20 g/hr, 66% of thioether being transformed.

Because this mercaptan boils at 98° C., compared with 150° C. for the tert-octyl mercaptan, the separation thereof is easy. The latter compound is reused for the production of a new charge of n-butyl tert-octyl sulfide for the purpose of a further reaction indicated above.

EXAMPLE 5

Sulfhydrolysis of isopropyl tert-butyl sulfide

The starting thioether is obtained by a reaction, catalyzed by sodium hydroxide, between tert-butyl mercaptan and isopropyl chloride.

The purpose of the sulfhydrolysis reaction is to transform the thioether to isopropylmercaptan and to tert-butylmercaptan according to the mechanism:

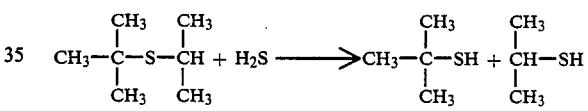

The conditions of Example 1 are adopted, that is, 110° C., 15 bar and 200 ml of AMBERLYST resin as catalyst. The hourly flow rate of thioether is 43.5 g and that of H₂S 45 g (that is, 4 H₂S per mole of thioether).

Isopropyl mercaptan is obtained with a selectivity of practically 100%, at a rate of 17.8 g/hr, 71% of thioether being transformed.

EXAMPLE 6

Sulfhydrolysis of omega-tert-butyl mercapto undecanoic acid

The acid-substituted sulfide reagent is prepared beforehand by reaction, catalyzed by sodium hydroxide, between tert-butylmercaptan and 11-bromo undecanoic acid. The sulfhydrolysis reaction permits the 11-mercapto undecanoic acid to be obtained and the tert-butylmercaptan to be recovered.

The reaction can be represented schematically as follows:

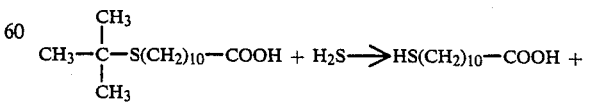

The conditions of Example 1 are adopted, in other words, 110° C., 15 bar and 200 ml of Amberlyst 15 resin as catalyst. The acid-substituted sulfide is introduced at a rate of 0.32 mole/hr in solution in heptane, while the H$_2$S is injected as a gas into the reactor on a basis of 1.30 mole/hr. A production of 41.8 g/hr of 11-mercapto undecanoic acid is obtained with a selectivity of practically 100%. The transformation of the starting acid-substituted sulfide is 60%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. A process for the production of mercaptans by reacting a thioether with hydrogen sulfide in the presence of an acid catalyst, wherein said thioether is an unsymmetrical thioether of the formula:

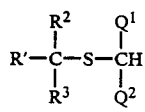

where the symbols R$^1$, R$^2$ and R$^3$, alike or different, are C$_1$–C$_{18}$ alkyl groups, Q$^1$ is an unsubstituted or COOH-substituted C$_1$–C$_{18}$ alkyl group, and Q$^2$ is a hydrogen atom or a C$_1$–C$_{18}$ alkyl group, said acid catalyst is selected from the aluminosilicates and the cation-exchange resins, the reaction being effected under a pressure of about 5 to 30 bars at a temperature between 80° and 200° C.

2. The process according to claim 1, wherein the thioether contains 6 to 24 carbon atoms and the temperature is between about 100° and 180° C.

3. The process according to claim 2, wherein the pressure is between 10 and 20 bars.

4. The process according to claim 1, wherein the proportion of H$_2$S used is from about 1 to 6 moles per mole of thioether.

5. The process according to claim 4, wherein the proportion of H$_2$S is from about 2 to 4 moles per mole of thioether.

6. The process according to claim 1, wherein the grouping R$^1$R$^2$R$^3$C is tert-butyl or tert-octyl.

7. The process according to claim 6, wherein the grouping CHQ$^1$Q$^2$ is n-butyl, n-dodecyl, isopropyl or (CH$_2$)$_{10}$COOH.

8. The process according to claim 1, wherein the tertiary mercaptan R$^1$R$^2$R$^3$C—SH formed is separated from the primary or secondary mercaptan Q$^1$Q$^2$CH—SH formed and is cyclically reused for preparing the starting thioether.

9. The process according to claim 8, wherein the starting thioether is prepared by reacting the tertiary mercaptan R$^1$R$^2$R$^3$C—SH with an olefin, a halogenated derivative or an alcohol.

10. The process according to claim 9, wherein the tertiary mercaptan is tert-butyl mercaptan or tert-octyl mercaptan and the olefin is 1-butene, 1-pentene or 1-dodecene.

11. The process according to claim 9, wherein the tertiary mercaptan is tert-butyl mercaptan and the halogenated derivative is isopropyl chloride or 11-bromo-undecanoic acid.

* * * * *